US008975607B2

(12) United States Patent
Renna et al.

(10) Patent No.: US 8,975,607 B2
(45) Date of Patent: Mar. 10, 2015

(54) CONFOCAL OPTICAL DETECTOR, DETECTOR ARRAY, AND MANUFACTURING METHOD THEREOF

(75) Inventors: Lucio Renna, Acireale (IT); Clelia Galati, San Gregorio di Catania (IT); Piero Giorgio Fallica, Catania (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 528 days.

(21) Appl. No.: 13/431,831

(22) Filed: Mar. 27, 2012

(65) Prior Publication Data

US 2012/0248347 A1 Oct. 4, 2012

(30) Foreign Application Priority Data

Apr. 1, 2011 (IT) .............. TO2011A0298

(51) Int. Cl.
*G01N 21/01* (2006.01)
*G02B 21/00* (2006.01)
*G01J 1/04* (2006.01)
*G01J 1/44* (2006.01)
*G01J 1/02* (2006.01)
*G01N 21/64* (2006.01)

(52) U.S. Cl.
CPC ........... *G02B 21/0032* (2013.01); *G01J 1/0437* (2013.01); *G01J 1/0411* (2013.01); *G01J 1/44* (2013.01); *G01J 1/0488* (2013.01); *G01J 1/0266* (2013.01); *G01N 21/6452* (2013.01)
USPC ......................................... 250/573; 359/385

(58) Field of Classification Search
CPC ..................................................... G02B 21/06

USPC ................... 250/573, 221; 356/239.1–239.5; 359/385
See application file for complete search history.

(56) References Cited

U.S. PATENT DOCUMENTS

| 3,013,467 | A | 12/1961 | Minsky |
| 6,690,511 | B2 | 2/2004 | Engelhardt et al. |
| 7,338,439 | B2 * | 3/2008 | Kanai ............................ 600/176 |
| 7,366,365 | B2 * | 4/2008 | Carver ............................ 385/12 |
| 7,366,394 | B2 * | 4/2008 | Takamatsu et al. ............ 385/147 |
| 7,382,449 | B2 * | 6/2008 | Peterman et al. ........ 356/139.04 |
| 2011/0291026 | A1 | 12/2011 | Renna et al. |

OTHER PUBLICATIONS

J. Stephen et al., *Applications of a semiconductor backscattered electron detector in a scanning electron microscope*, Journal of Physics E: Scientific Instruments, vol. 8, pp. 607-610, 1975.
P. Buzhan et al., *Silicon photomultiplier and its possible applications*, Nuclear Instruments and Methods in Physics Research Section A, vol. 504, pp. 48-52, 2003.

* cited by examiner

*Primary Examiner* — Seung C Sohn
(74) *Attorney, Agent, or Firm* — Seed IP Law Group PLLC

(57) ABSTRACT

A confocal optical detector including a light source generating a first optical beam along an axis; an optoelectronic sensor; an optical focusing device, which receives and focuses the first optical beam; and a hole, which receives the first optical beam and is arranged between the optoelectronic sensor and the optical focusing device. The optoelectronic sensor is arranged between the light source and the hole. In addition, the optoelectronic sensor and the optical focusing device are aligned along the axis.

20 Claims, 13 Drawing Sheets

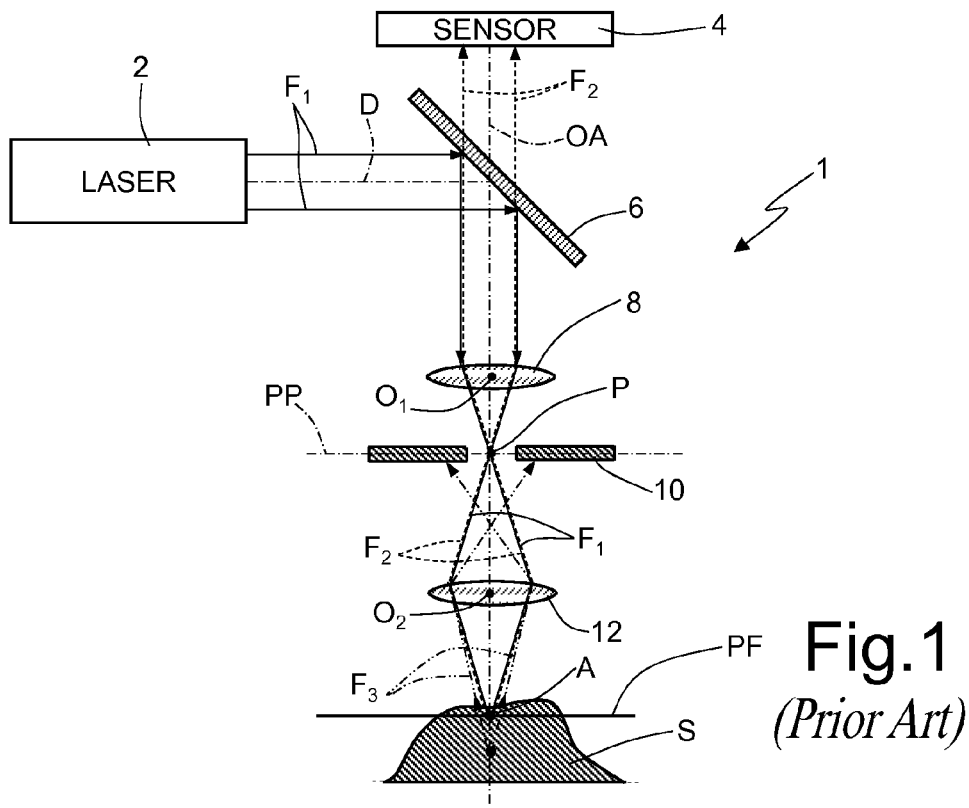
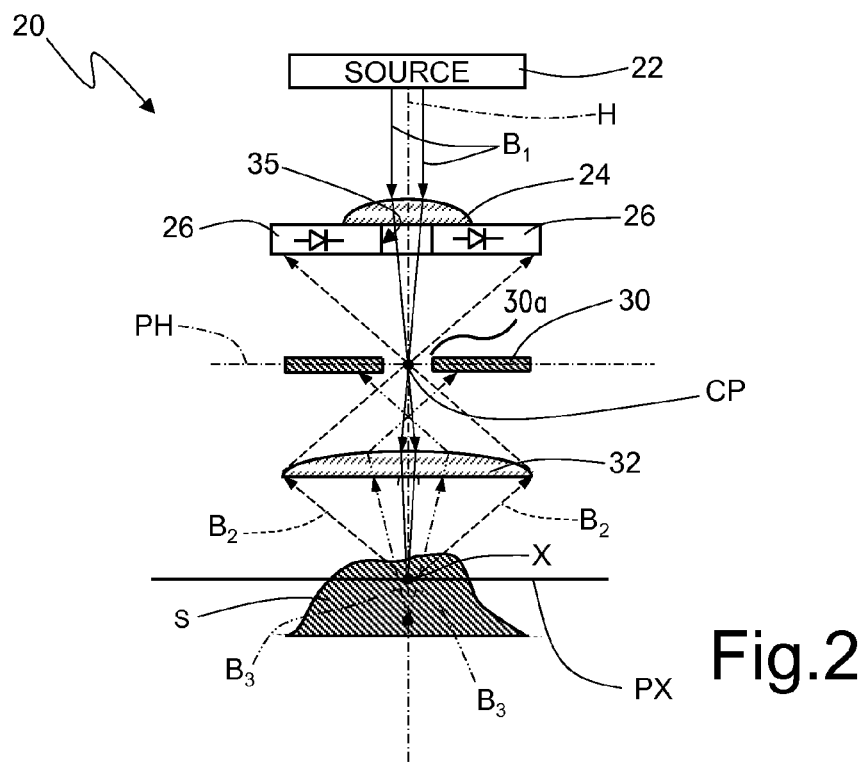
Fig.1
(Prior Art)
Fig.2

CONFOCAL OPTICAL DETECTOR, DETECTOR ARRAY, AND MANUFACTURING METHOD THEREOF

BACKGROUND

1. Technical Field

The present disclosure relates to a confocal optical detector, to a detector array, and to a manufacturing method thereof.

2. Description of the Related Art

As is known, today available are light detectors, even miniaturized ones, as well as microanalyzers, the latter being also known as "micro-scanners".

In general, light detectors enable scanning of small portions of specimens to be analyzed in order to determine characteristics and/or properties of the specimens. For the above purpose, light detectors, also known as "optical detectors", usually comprise optical elements and movement devices having particularly small dimensions, for example of the order of some millimeters. In addition, optical detectors have been proposed, in which the movement devices are formed by microelectromechanical systems (MEMS).

In general, optical detectors envisage illuminating with a first light beam a portion of a specimen, and then receiving and analyzing a second light beam coming from the specimen itself, whether generated by reflection of the first light beam by the specimen or else by excitation of the specimen following upon the incidence of the first light beam. In the latter case, they are commonly referred to as optical detectors based upon the phenomenon of light-induced fluorescence, or else, more briefly, as "fluorescence detectors".

Irrespective of the details of construction, optical detectors find wide use in sectors such as, for example, diagnostics for purposes of medical research. For example, in diagnostic field it is known to couple optical detectors to diagnostic devices.

In general, the diagnostic devices each include a respective assay. In turn, the assay may comprise a solid substrate, which is typically of a flat type and has a surface that is functionalized so as to present detection areas, within which receptors provided with specific markers, described hereinafter, are immobilized.

In practice, by "receptor" is meant any member of a pair or of an n-tuple of elements that can bind together. Consequently, each receptor is able to couple, or in any case react, with a respective binding mate, or else with a respective plurality of binding mates, enabling detection thereof. For example, the receptors may comprise biomolecules (DNA, RNA, proteins, antigens, antibodies, aptenes, sugars, etc.) or chemical species, or micro-organisms or parts of them (bacteria, viruses, spores, cells, etc.).

As regards the markers, each of them is such that, when the corresponding receptor couples or interacts with its own binding mate, or else with its own binding mates, it is activated. In particular, in the so-called fluorescence diagnostic devices, if an activated marker is excited with a light radiation at a certain wavelength $\lambda_e$, it emits a light radiation of its own having a wavelength $\lambda_f$ different from the wavelength $\lambda_e$. In general, these markers are known as "fluorescence markers".

By way of example, known to the art are three-component binding assays, which use, each, a first immobilization of a first antibody to a solid substrate, this first antibody being able to couple with an antigen present in a specimen solution. Coupling with the antigen is then detected thanks to a second antibody, which functions as the marker and couples with a different epitope of the same antigen. The second antibody has a fluorescent label attached thereto; consequently, the amount of fluorescence is correlated to the amount of antigens present in the specimen solution.

In practice, by detecting, by means of an appropriate optical detector, the light radiation at the wavelength $\lambda_f$, it is possible to derive information on the chemico-physical characteristics of the specimen to be analyzed, since the light intensity detected is a function of the amount of markers activated in the assay, and hence of the amount of molecules or biomolecules detected from the assay. For the above purpose, the optical detector must be sensitive to the wavelength $\lambda_f$ of the light radiation emitted by the markers.

This being said, optical detectors are known that are particularly suited for detection of the electromagnetic radiation emitted by markers, especially by fluorescent markers.

In particular, known to the art are the so-called "confocal detectors", as described, for example, in U.S. Pat. No. 3,013,467 and a principle diagram of which is shown in FIG. 1.

In detail, a confocal detector 1, also known as "confocal microscope", is formed by a laser source 2, by an optoelectronic sensor 4, by an optical beam splitter 6, by a first lens 8, by a so-called "pinhole" 10, and by a second lens 12. FIG. 1 moreover shows an element to be analyzed S, which may be formed by an assay on which a specimen to be analyzed has been laid.

In greater detail, the pinhole 10 and the first and second lenses 8, 12 are optically aligned; i.e., they have substantially coinciding optical axes, which hence define a system axis OA. In practice, assuming for simplicity that the first and second lenses 8, 12 are thin and have, respectively, a first optical center $O_1$ and a second optical center $O_2$, the first and second optical centers $O_1$, $O_2$ lie along the system axis OA. In addition, P is the center of the pinhole 10, which also lies along the system axis OA. Furthermore, the pinhole 10 is arranged between the first lens 8 and the second lens 12.

The optoelectronic sensor 4 is usually aligned with respect to the system axis OA. Moreover, the optical beam splitter 6 also intercepts the system axis OA and is arranged between the optoelectronic sensor 4 and the pinhole 10.

As regards, instead, the laser source 2 and the element to be analyzed S, the laser source 2 is arranged laterally with respect to the system axis OA, whilst the element to be analyzed S intercepts the system axis OA, with respect to which it is substantially aligned.

In greater detail, the laser source 2 and the optical beam splitter 6 are arranged in such a way that, if we refer to the "first optical beam $F_1$" to indicate the electromagnetic radiation emitted of the laser source 2, the first optical beam $F_1$ propagates from the laser source 2 in a first direction of propagation D, until it impinges upon the optical beam splitter 6, which reflects a first portion thereof in the direction of the first lens 8, along the system axis OA. In particular, the first direction of propagation D forms an angle of 90° with the system axis OA. Hence, if the portion reflected by the optical beam splitter 6 is once again referred to as "first optical beam $F_1$" (i.e., if we neglect the portion of first optical beam $F_1$ that is not reflected by the optical beam splitter 6), the first optical beam $F_1$ follows an optical path that forms an angle of 90°.

After is has been reflected by the optical beam splitter 6, the first optical beam $F_1$ is focused by the first lens 8 at the center P of the pinhole 10, and then propagates until it impinges on the second lens 12, which focuses it on an image point A, which is arranged at the intersection of the system axis OA with an image plane PF of the second lens 12 itself.

In practice, in order to get the first optical beam $F_1$ to follow the path described, and assuming for simplicity that the first and second lenses 8, 12, in addition to being thin, are biconvex, the center P of the pinhole 10 and the image point A are conjugate points; i.e., if we assume setting, in absence of the element to be analyzed S, a pointlike object in the image point A, it forms a corresponding image at the center P of the pinhole 10, and moreover, if we assume setting this pointlike object at the center P of the pinhole 10, it forms a corresponding image in the image point A. Once again in other words, if PP is the plane of the pinhole 10, orthogonal to the system axis OA and containing the center P, the plane PP of the pinhole 10 and the image plane PF of the second lens 12 are conjugate planes of the second lens 12. This explains why the confocal detector 1 is referred to as "confocal".

Operatively, in the case where in the image point A an activated marker is present, when it is illuminated by the first optical beam $F_1$, it generates a second optical beam $F_2$; the first and second optical beams $F_1$, $F_2$ may have, respectively, the wavelength $\lambda_e$ and the wavelength $\lambda_f$.

The second optical beam $F_2$ propagates from the image point A up to the second lens 12, by which it is focused at the center P of the pinhole 10. Next, the second optical beam $F_2$ propagates through the first lens 8 and the optical beam splitter 6, until it impinges on the optoelectronic sensor 4. In particular, as regards the optical beam splitter 6, it exhibits a dichroic behavior, i.e., albeit reflecting at least in part radiation at the wavelength $\lambda_e$, is transparent for radiation having wavelength $\lambda_f$; hence, it does not interfere with the second optical beam $F_2$.

The optoelectronic sensor 4 is hence able to detect and process the second optical beam $F_2$, on the basis of which it determines chemico-physical characteristics of the element to be analyzed S. In particular, thanks to the presence of the pinhole 10, on the optoelectronic sensor 4 there impinge, to a first approximation, only optical rays that, in addition to forming the second optical beam $F_2$, are originated exactly from the portion of the element to be analyzed S present in the image point A. In fact, any possible other optical rays (designated by F3 in FIG. 1) generated by portions of the element to be analyzed S that are arranged in points different from the image point A, are filtered by the pinhole 10 before reaching the first lens 8, and hence do not reach the optoelectronic sensor 4. This prevents formation of so-called "artifacts", i.e., spurious light signals generated by points other than the image point A, for example points arranged at the intersection of the system axis OA with planes parallel to the image plane PF of the second lens 12, which could cause a deterioration of the performance of the confocal detector 1.

If the confocal detector 1 is equipped with an appropriate device (not shown) for movement of the element to be analyzed S, it hence makes it possible to obtain three-dimensional images of the element to be analyzed S, enabling a fast and effective analysis of the specimen to be analyzed S itself. Alternatively, and once again for this purpose, the confocal detector 1 may be equipped with a system for movement of at least one component thereof, such as, for example, the optical beam splitter 6.

Even though the confocal detector 1 is hence suited to the analysis of specimens, on account of the optical paths followed by the first and second optical beams $F_1$ and $F_2$ it is not easy to use in the case where a detector array is to be provided, i.e., a matrix of confocal detectors coplanar to one another. In fact, the overall dimensions of the confocal detector 1 may prove excessive for this kind of applications.

BRIEF SUMMARY

One embodiment of the present disclosure is directed to a confocal optical detector that includes an axis, a light source configured to generate a first optical beam along the axis, an optoelectronic sensor aligned along the axis, an optical focusing device configured to receive and focus the first optical beam, the optical focusing device being aligned with the optoelectronic sensor along the axis, and an opaque layer having a hole, the hole being configured to receive the first optical beam, the layer being arranged between the optoelectronic sensor and the optical focusing device, and the optoelectronic sensor being arranged between the light source and the layer.

BRIEF DESCRIPTION OF THE SEVERAL VIEWS OF THE DRAWINGS

For a better understanding of the present disclosure, embodiments thereof are now described, purely by way of non-limiting example, with reference to the attached drawings, wherein:

FIG. 1 shows a simplified block diagram of a confocal detector of a known type;

FIG. 2 shows a simplified block diagram of the present optical detector;

DETAILED DESCRIPTION

Figure 3:
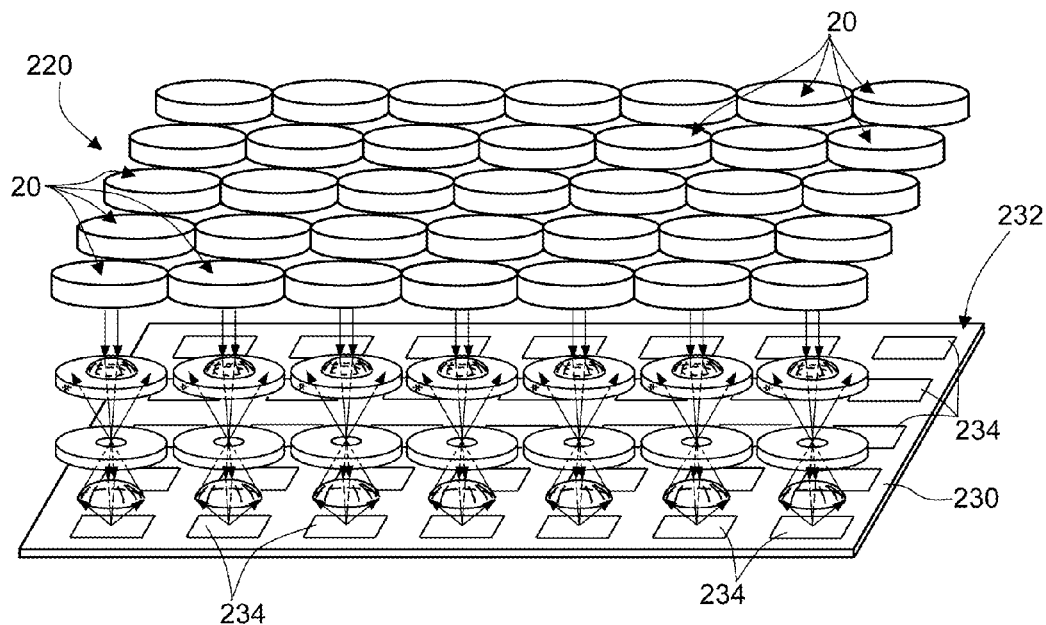
FIG. 3 is a schematic perspective view of an array of optical detectors set on top of an assay.

FIG. 2 shows an example of embodiment of an optical detector 20 of a confocal type. In detail, as illustrated in FIG. 3, the optical detector 20 may belong, for example, to an array 220 of optical detectors 20, which may comprise any number of optical detectors 20. By way of clarification, FIG. 3, which will be described in greater detail hereinafter, shows also an assay 230 of a known type, which has a top surface 232 functionalized so as to present a plurality of detection areas 234, immobilized inside which are receptors provided with markers (not shown).

Once again with reference to FIG. 2, the optical detector 20 comprises a light source 22, a first lens 24, an optoelectronic sensor 26, a pinhole 30a through an opaque layer 30, and a second lens 32, arranged in succession and aligned.

In detail, the light source 22 is formed, for example, by a laser source, which emits a radiation that is to a first approximation monochromatic at a first wavelength $\lambda_1$. In what follows, for reasons of brevity, the radiation emitted by the light source 22 will be referred to as "first optical beam $B_1$".

In greater detail, the optical axes of the first and second lenses 24, 32 coincide and define a system axis H. In addition, the pinhole 30a of the layer 30 lies in a plane PH orthogonal to the system axis H, has a center CP, which lies along the system axis H, and may have a diameter, for example, of 1 µm. In addition, the first and second lenses 24, 32 may be both, for example, plane-convex, with convexity facing towards the light source 22 and with the respective plane sides arranged perpendicular to the system axis H.

The optoelectronic sensor 26 and the light source 22 are arranged so as to intercept the system axis H, and are orthogonal thereto. In particular, the light source 22 emits the first optical beam $B_1$ along the system axis H. In addition, the optoelectronic sensor 26 defines a sensor opening 35, for example, of a cylindrical shape with a base having a diameter of 20 µm, the axis of which coincides with the system axis H. In addition, as has been mentioned previously, the light source 22 and the optoelectronic sensor 26 are arranged in such a way that the first lens 24 is arranged between the light source 22 and the optoelectronic sensor 26, which, in turn, is arranged between the first lens 24 and the pinhole 30a. Purely by way of example, in the embodiment shown in FIG. 2, the first lens 24 is arranged in direct contact with the optoelectronic sensor 26. In particular, the plane side of the first lens 24 is arranged on top of, and in direct contact with, the optoelectronic sensor 26.

In greater detail, the light source 22 is arranged in such a way that the first optical beam propagates along the system axis H, until it impinges on the first lens 24, which focuses it at the center CP of the pinhole 30a. In particular, the first lens 24 focuses the first optical beam $B_1$ in such a way that it traverses the sensor opening 35 without interfering with, i.e., without being reflected or absorbed by, the optoelectronic sensor 26.

After it has been focused at the center CP of the pinhole 30a, where it assumes the minimum spot size, the first optical beam $B_1$ propagates in the direction of the second lens 32, progressively increasing its own spot size. Next, the second lens 32 focuses the first optical beam $B_1$ in an image point X, which is arranged at the intersection between the optical axis of the second lens 32, and hence the system axis H, and an image plane PX of the second lens 32 itself.

In greater detail, the second lens 32 and the pinhole 30a are such that the center CP of the pinhole 30a and the image point X are conjugate points with respect to the second lens 32. In other words, if we assume setting a pointlike object in the image point X, it forms a corresponding image at the center CP of the pinhole 30a. Moreover, if we assume setting the pointlike object at the center CP of the pinhole 30a, it forms a corresponding image in the image point X.

In practice, if the second lens were biconvex and thin, if p and q are the distances from the optical center of the second lens 32 respectively of the center CP of the pinhole 30a and of the image point X, and f is the focal length of the second lens, we would have $1/p + 1/q = 1/f$. Instead, with specific reference to the embodiment shown in FIG. 2, where the second lens 32, which is not necessarily thin, is plane-convex, and hence is formed, as shown in greater detail in FIG. 4, by a plane surface 32a and by a curved surface 32b, the distances of the center CP and of the image point X from the second lens 32 change, in a way in itself known. In particular, if we assume that the curved surface 32b defines a portion of sphere of radius r, and we designate by 32c a top point of the second lens 32, which is the point of the second lens 32 closest to the center CP of the pinhole 30a, i.e., the point that is located at the intersection between the curved surface 32b and the system axis H, we have that the center CP of the pinhole 30a is at a distance from the top point 32c equal to four times the radius r. Moreover, the top point 32c is in turn at a distance from the image point X equal to four times the radius r.

In general, it is in any case always possible to determine the mutual position of the center CP and of the image point X with respect to the second lens 32, in such a way that the center CP of the pinhole 30a and the image point X are conjugate points of the second lens 32, whatever the shape of the second lens 32. On the other hand, the second lens 32 could also be replaced by an optical assembly formed by a number of lenses.

This being said, in the case where, at the image point X, there is present an activated marker of an element to be analyzed S (FIG. 2), the marker is excited by the first optical beam $B_1$, and hence generates a second optical beam $B_2$, formed by a radiation that to a first approximation is monochromatic at a second wavelength $\lambda_2$.

Figure 4:
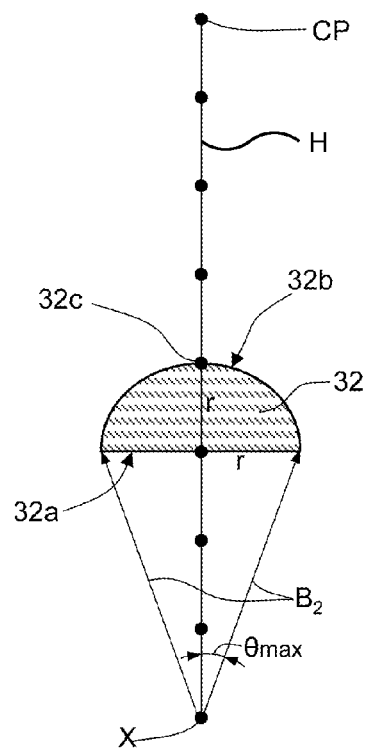
FIG. 4 shows a geometrical scheme representing distances between components of the present optical detector.

As shown in greater detail in FIG. 4, if we assume that the second optical beam $B_2$ is emitted by the activated marker with an angle of divergence θ not greater than a limit angle $\theta_{max}$, i.e., if we assume that the second optical beam $B_2$ is formed by optical rays that propagate starting from the image point X forming with the system axis H angles having amplitude not greater than the limit angle $\theta_{max}$, the entire second optical beam $B_2$ is collected by the second lens 32, and in particular by the plane surface 32a of the second lens 32.

Purely by way of example, if NA is the numeric aperture of the second lens 32 and $n_{ex}$ is the refractive index of the medium arranged between the second lens 32 and the element to be analyzed S, we have approximately $NA = n_{ex} \cdot \sin(\theta_{max})$. In the case where the medium arranged between the second lens 32 and the element to be analyzed S is air, we have $n_{ex}=1$; consequently, if we assume, for example, NA=0.5, we obtain a limit angle $\theta_{max}$ of approximately 30°.

Once again with reference to FIG. 2, the second optical beam $B_2$ is then focused by the second lens 32 at the center CP of the pinhole 30a, where it assumes the minimum spot size. Next, the second optical beam $B_2$ propagates until it reaches the optoelectronic sensor 26, assuming a progressively increasing spot size with respect to the minimum spot size assumed at the center CP of the pinhole 30a.

Figure 5:
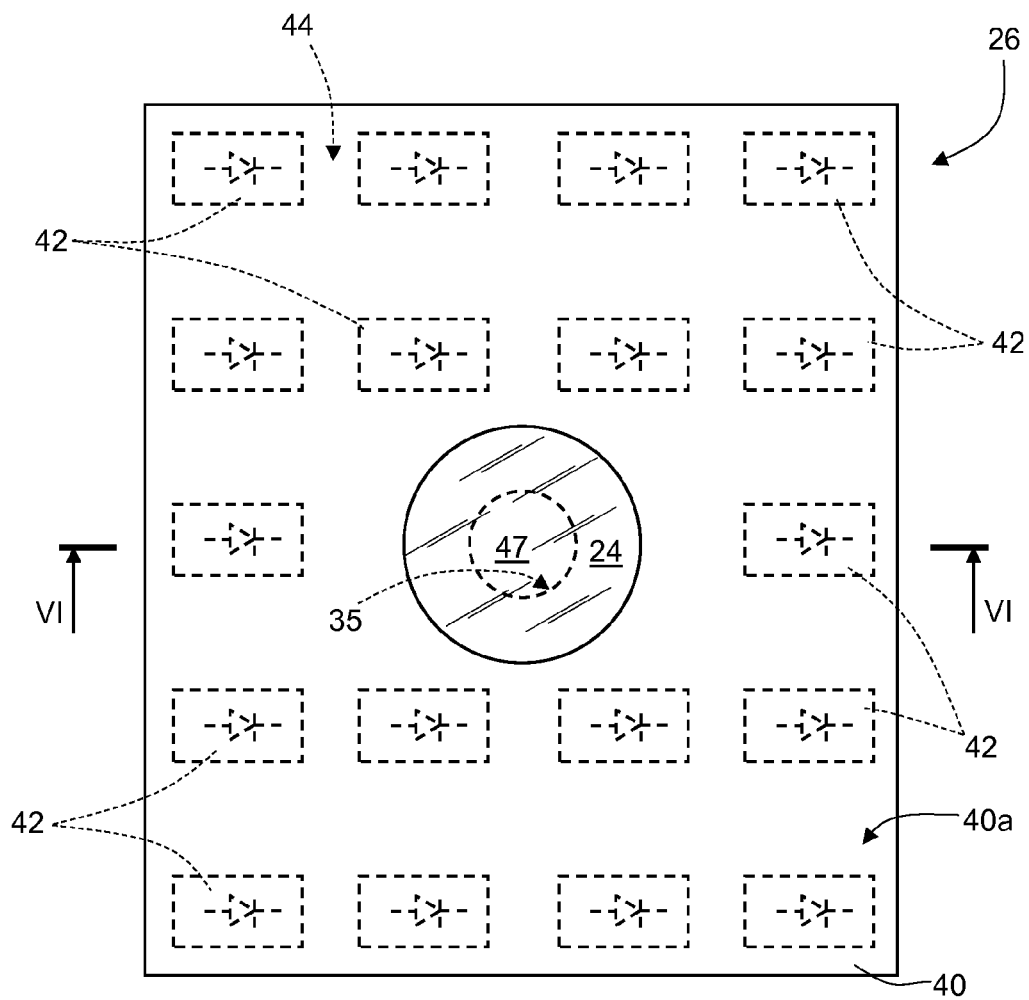
FIG. 5 is a schematic top plan view of an optoelectronic sensor of the optical detector shown in FIG. 2.

As shown in greater detail in FIG. 5, the optoelectronic sensor 26 may be formed within a die 40 of semiconductor material, having a circular or polygonal shape, in top plan view, formed inside which is a plurality of photodiodes. In particular, in the embodiment shown in FIG. 5, the die 40 has a rectangular shape, in top plan view. In addition, the side of the die 40 may have a length of the order of some tens of micrometers.

Formed within the die 40 is a plurality of Geiger-mode avalanche photodiodes 42, also known as "single-photon avalanche diodes" (SPADs), which, as a whole, form a silicon photomultiplier (SiPM) 44.

Figure 6:
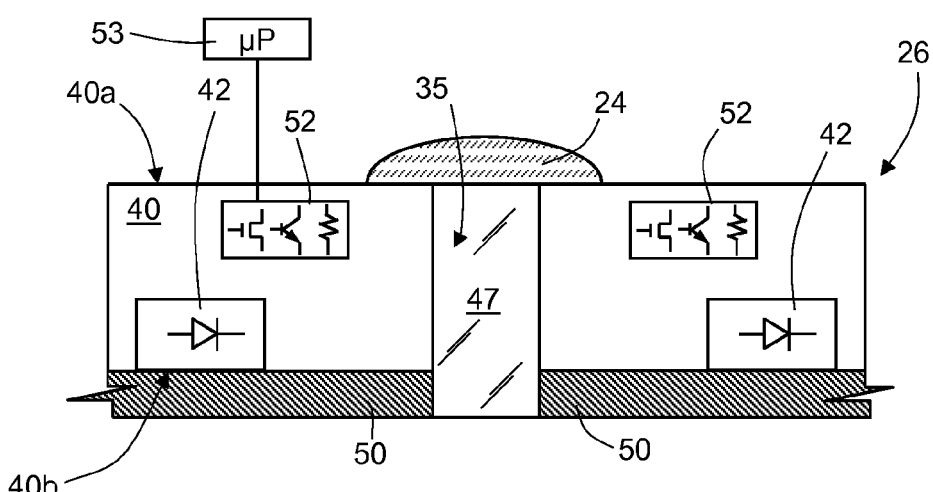
FIG. 6 is a schematic cross-sectional view of the optoelectronic sensor shown in FIG. 5, taken along the line of section VI-VI shown in FIG. 5.

More in particular, as shown in FIG. 6, the die 40 has a first surface 40a, facing the source 22, and a second surface 40b, facing the layer 30. Moreover, the SPADs 42 a positioned adjacent to the second surface 40b, which is hence a sensitive surface of the optoelectronic sensor 26. In practice, since the optoelectronic sensor 26 is aligned to the system axis H, the sensitive surface 40b is set perpendicular with respect to the system axis H.

Underneath the second surface 40b, and in contact therewith, there may moreover be present an optical filter 50, such as, for example, a Bragg filter, which is transparent for radiation at the second wavelength $\lambda_2$, but filters radiation at the first wavelength $\lambda_1$.

In greater detail, the sensor opening 35 passes also through the optical filter 50, which extends underneath each SPAD 42. Moreover, the sensor opening 35 may be empty, or else, as in the case of the embodiment shown in FIGS. 5 and 6, may be filled by a transparent region 47, which is substantially transparent to the first optical beam $B_1$ and is overlaid, in direct contact, by the first lens 24, which on the other side extends at least in part on top of the first surface 40a, with which it is in direct contact. In practice, as shown once again in FIG. 6, the transparent region 47 may extend in part underneath or past the second surface 40b so as to be surrounded at least in part by the optical filter 50.

Purely by way of example, the transparent region 47 may be formed with through-silicon-via (TSV) technology, which, as is known, envisages the iteration of plasma etches.

Moreover formed within the die 40 is an electronic processing circuit 52, which is electrically connected (connection not shown) to the SPADs 42 and has the function of processing electrical signals generated by the SPADs 42 following upon reception of the second optical beam $B_2$. The electronic processing circuit 52 may moreover be electrically connected to an electronic processing system 53, external to the optical detector 20.

In practice, when the optoelectronic sensor 26 receives the second optical beam $B_2$, the SPADs 42 and the electronic processing circuit 52 operate in a way in itself known. In particular, the electronic processing circuit 52 supplies to the electronic processing system 53 image signals, generated on the basis of the electrical signals supplied by the SPADs 42.

From an optical standpoint, thanks to the presence of the pinhole 30a, basically, the second optical beam $B_2$ does not contain optical contributions (radiation) emitted by markers arranged in points different from the image point X. In fact, these possible optical contributions, or rather the corresponding optical rays, after traversing the second lens 32, do not pass through the pinhole 30a. An example of these optical rays, which are designated by $B_3$, is shown qualitatively in FIG. 2. Even in the case where some of said optical rays were to pass through the pinhole 30a, they would be filtered by the optical filter 50 before reaching the SPADs 42.

Consequently, the optical detector 20 presents the same advantages as traditional confocal receivers in terms of quality of the images and of the possibility of making three-dimensional scans of the assays. Moreover, since the light source 22, the optoelectronic sensor 26, and the second lens 32, as well as the pinhole 30a of the layer 30, are arranged aligned, the optical detector 20 is characterized by small overall dimensions, and hence can be integrated with greater ease. It can thus form arrays of high-density optical receivers, in which a large number of optical detectors are formed within an area of small dimensions.

In other words, thanks to the axial arrangement of the light source 22, of the optoelectronic sensor 26, and of the second lens 32, the first and second optical beams $B_1$, $B_2$ propagate along the system axis H, and thus follow optical paths that are substantially parallel and coincident, without the need for any of them to form an angle of 90°.

Figure 7:
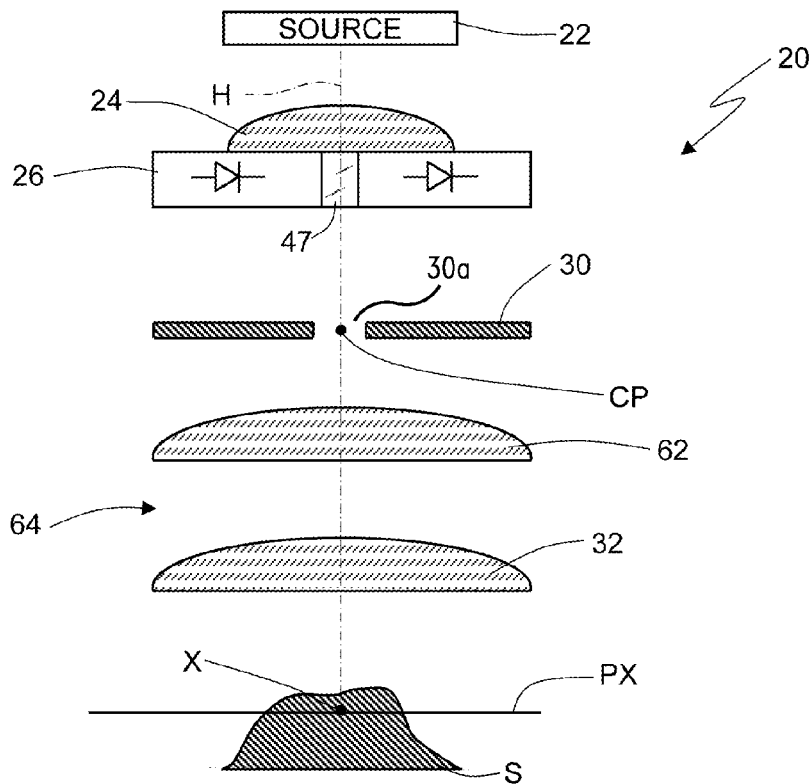
FIGS. 7 and 8 are simplified blocks diagrams of variants of the optical detector shown in FIG. 2.

As shown in FIG. 7, in order to improve the optical performance of the optical detector 20, in particular as regards the immunity to phenomena such as, for example, spherical aberration, moreover possible are embodiments in which a third lens 62 is present, which is for example the same as the second lens 32, arranged between the pinhole 30a of the layer 30 and the second lens 32. In greater detail, also the third lens 62 has a convexity facing the pinhole 30a, and moreover has its optical axis that coincides with the system axis H.

In practice, the second and third lenses 32, 62 form an optical assembly 64. In addition, the second and third lenses 32, 62 are arranged in such a way that the center CP of the pinhole 30a and the image point X are conjugate points of the optical assembly 64. In this way, the image of a hypothetical pointlike object set in the image point X is formed once again at the center CP of the pinhole 30a.

Figure 8:
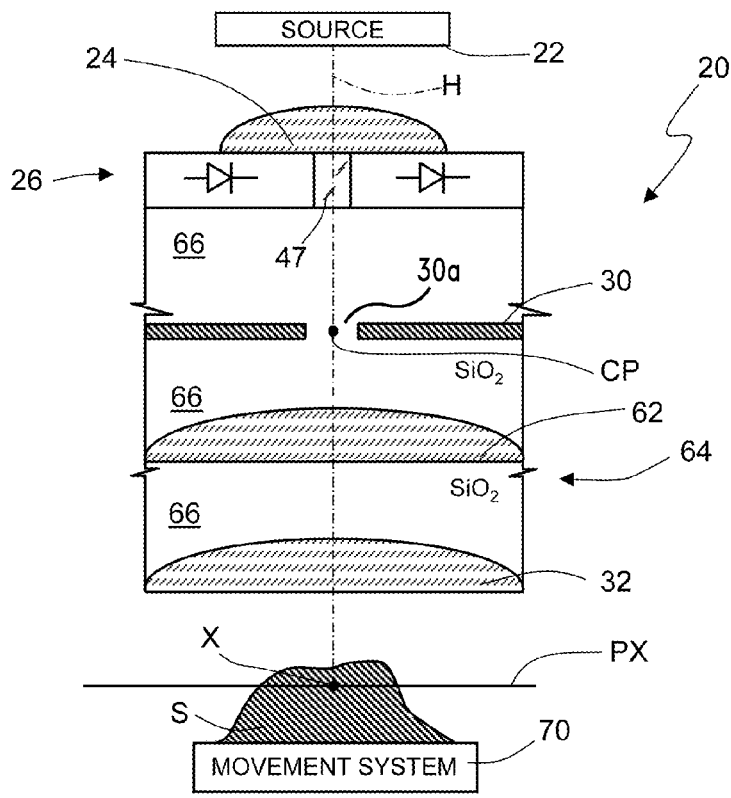

In the embodiments shown in FIGS. 2 and 7, air is present between the optoelectronic sensor 26, the pinhole 30a, and the second lens 32 (and the third lens 62, if present). However, as shown in FIG. 8, embodiments are possible in which the optoelectronic sensor 26, the pinhole 30a, and the second lens 32 are formed within a dielectric region 66, transparent both for the first wavelength $\lambda_1$ and for the second wavelength $\lambda_2$ and made, for example, of silicon oxide $SiO_2$. In practice, as shown precisely in FIG. 8, which, without this implying any loss of generality, refers to the case where also the third lens 62 is present, the optoelectronic sensor 26, the pinhole 30a of the layer 30, and the second lens 32, as well as the third lens 62, are formed in a monolithic way. Purely by way of example, in this embodiment, the second and third lenses 32, 62 may be made, for example, of antimony trioxide $Sb_2O_3$. In this case, the presence of silicon oxide, instead of air, leads to modifications in the arrangement of the pinhole 30a and of the optical assembly 64 in order to guarantee that the center CP of the pinhole 30a is still a conjugate point of the image point X with respect to the optical assembly 64.

As shown with reference, by way of example, to the embodiment represented in FIG. 8, it is moreover possible for the optical detector 20 to include a movement system 70, which is designed to move the element to be analyzed S with respect to the image point X of the optical detector 20. In this case, the processing system 53 (FIG. 6) is able to carry out a three-dimensional scan of the element to be analyzed S.

Figure 9:
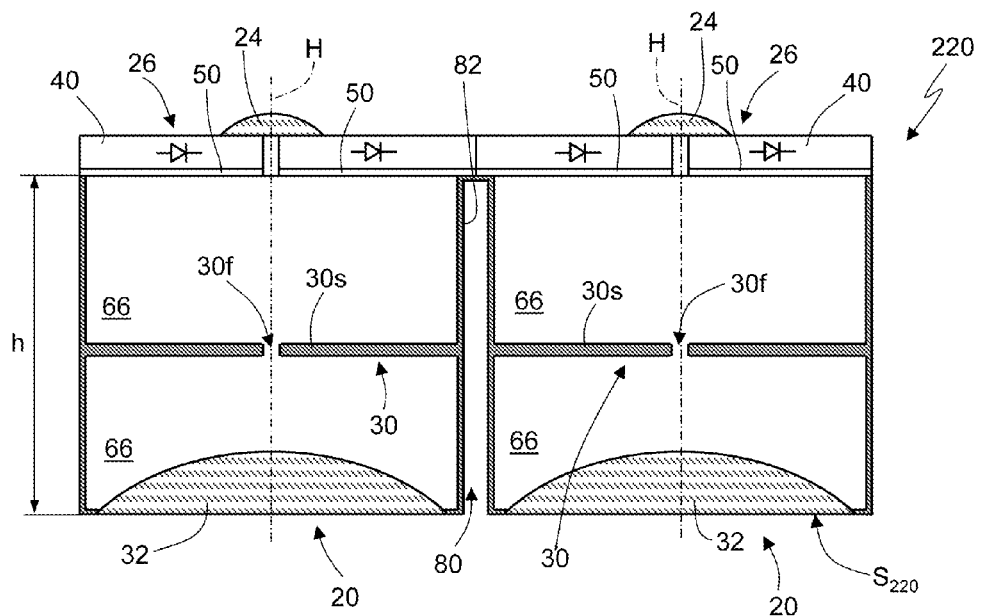
FIG. 9 is a schematic cross section of a portion of an array of optical detectors.

As regards the array 220 of optical detectors 20, it is possible, as shown in FIG. 9, for the optical detectors 20 of the array itself to be formed in a monolithic way. In particular, FIG. 9 shows two optical detectors 20, which, without this implying any loss of generality, are without the third lens 62. For simplicity of representation, not shown FIG. 9 are the light sources 22 of the two optical detectors 20, which can be provided apart with respect to what is shown in FIG. 9 itself.

In greater detail, the two optical detectors 20 are both formed within the die 40; more precisely, the electronic processing circuits and the SPADs (not shown in FIG. 9) of said two optical detectors 20 are formed within the die 40, which may be adjacent to the optical filter 50.

In practice, the two optical detectors 20 are arranged in such a way that the respective system axes H are parallel to one another. Moreover, the two adjacent optical detectors 20 are separated by a trench 80. In particular, if h is the distance that separates the optical filter 50 from the plane surfaces of the second lenses 32, which define a bottom surface $S_{220}$ of the array 220, the trench 80 extends vertically with a thickness equal to h and is open at the bottom, i.e., in a region corresponding to the bottom surface $S_{220}$ of the array 220. In addition, the trench 80 is internally coated by an opaque coating 82, made, for example, of metal material, and consequently performs the function of optically decoupling the two optical detectors 20. Once again, the opaque coating 82 is connected to the layer 30 in which the pinhole 30a of the two optical detectors 20 is formed. More precisely, each pinhole 30a is formed by a shielding portion 30s of the layer 30 which has a hole 30f (having, for example, a circular shape) defined by the shielding portion 30s.

Figure 10:
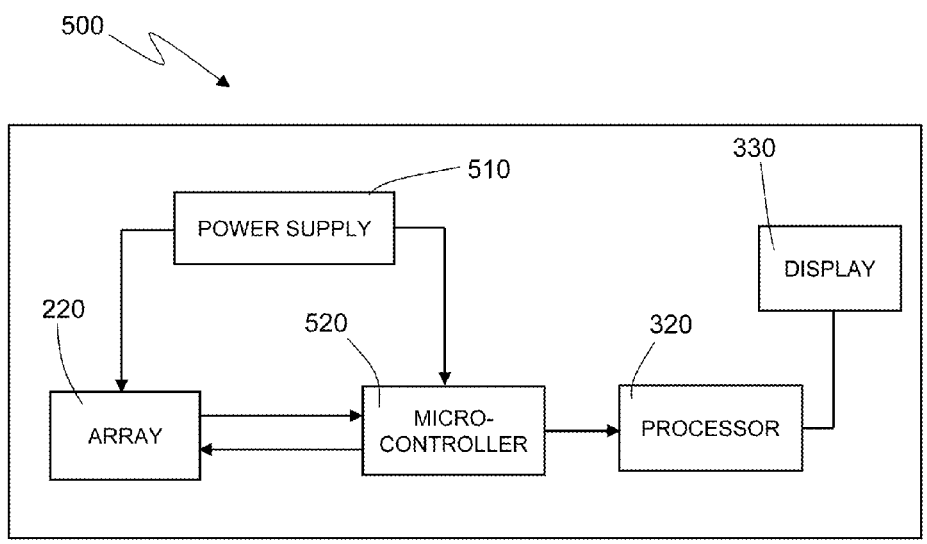
FIG. 10 shows a block diagram of a system that uses an array of optical detectors.

The array 220 of optical detectors 20, whether monolithic or not, can be used in a generic optoelectronic analysis system 500 of the type shown in FIG. 10, where a power supply 510 supplies the array 220 of optical detectors 20 and at least one microcontroller 520 connected to the array 220 itself. The microcontroller 520 processes the signal output from the array 220, formed in the case in point by the image signals supplied by the electronic processing circuits 52 of the optical detectors 20, and supplies a processed signal to a processor 320, which enables analysis of this processed signal and display of the information associated to this processed signal on a display 330.

Figure 11:
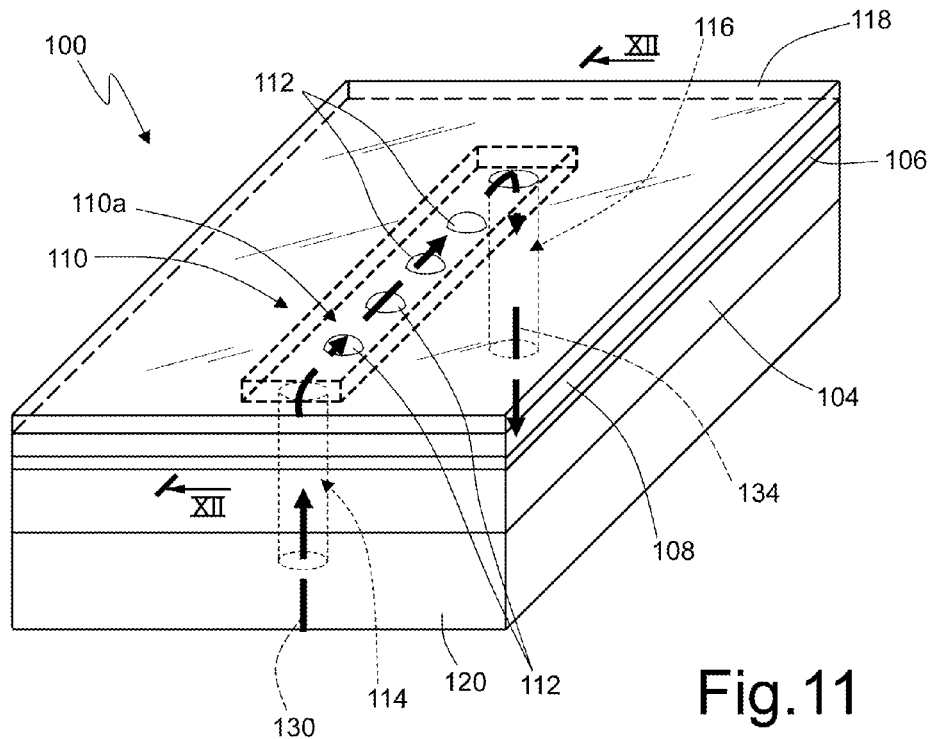
FIG. 11 is a perspective view of a diagnostic device.

Purely by way of example, the array 220 of optical detectors 20 can find an advantageous use if coupled to a diagnostic device 100 of a microfluidic type, for example of the type described in the Italian patent application TO2010A000437 filed on May 25, 2010, which corresponds to U.S. Patent Publication No. 2011/0291026, which is hereby incorporated by reference in its entirety. An example of the diagnostic device 100 is shown in FIG. 11 and is shown as part of an embodiment of the present disclosure in FIG. 12.

In detail, the diagnostic device 100 comprises a substrate 104 of semiconductor material, for example silicon, and a compatible layer 106, made, for example, of silicon oxide ($SiO_2$) and arranged on top of, and in direct contact with, the substrate 104; in turn, the substrate 104 is arranged on a support 120, made, for example, of plastic material (for example, polycarbonate). The compatible layer 106 is, in particular, a compatible layer with an assay and with the receptors used in the diagnostic device 100 themselves (described hereinafter), i.e., a layer that does not alter the nature of these receptors. As an alternative to the compatible layer 106, a non-biocompatible layer (not shown) appropriately passivated may be present.

The diagnostic device 100 further comprises a structural layer 108, made, for example, of photoresist with a base of acrylic polymers and arranged on top of, and in direct contact with, the compatible layer 106. The structural layer 108 has a channel 110 formed by means of selective removal of portions of the structural layer 108, until the compatible layer 106 is reached and exposed. In this way, the bottom of the channel 110 is formed by the compatible layer 106, whereas the side walls of the channel 110 are formed by the structural layer 108.

In greater detail, designating by 110a a bottom surface of the channel 110, which defines the bottom of the channel 110 and has a rectangular shape, in top plan view, this is surrounded on all four sides by the structural layer 108. For example, the bottom surface 110a of the channel 110 may have a length of approximately 1 mm, and a width of approximately 200 μm.

Figure 13:
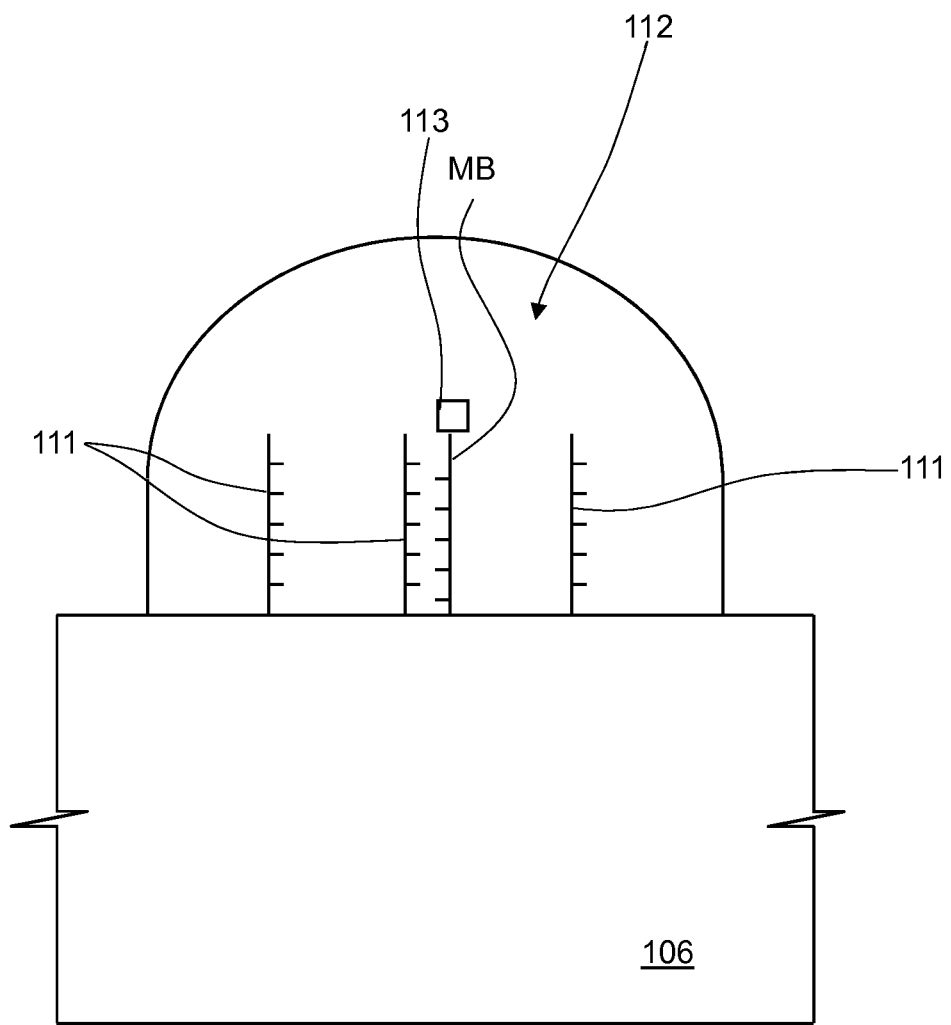
FIG. 13 is a schematic cross section of a portion of the diagnostic device shown in FIGS. 11 and 12.

The channel 110 houses one or more detection regions 112, for example in the form of "spots" arranged in series along the channel 110 and separated from one another by a distance of approximately 100 μm, each of which, as shown in FIG. 13, comprises receptors 111, for example formed by biomolecules and deposited in a known way.

The diagnostic device 100 further comprises an inlet hole 114 and an outlet hole 116, formed through the substrate 104, the compatible layer 106, and the support 120, and designed to form, respectively, an access path (see the arrow 130) from outside the diagnostic device 100 towards the channel 110 and an outlet path (see the arrow 134) from the channel 110 towards the outside of the diagnostic device 100.

The diagnostic device 100 further comprises a cover layer 118 arranged on top of the structural layer 108, so as to seal the channel 110 at the top, in a hermetic way. In this way, the only points of access to the channel 110 are the inlet hole 114 and the outlet hole 116. The cover layer 118 is made of a material transparent to light (or, in any case, transparent to the first and second wavelengths $\lambda_1$, $\lambda_2$). In this way, the channel 110 is completely accessible optically from outside the diagnostic device 100. For example, the cover layer 118 may be an adhesive tape or an adhesive film, or again a layer of material rendered adhesive and arranged on top of the channel 110 so as to seal it.

In practice, through the inlet hole 114, it is possible to cause a specimen to be analyzed to flow along the entire channel 110 (see the arrow 132 in FIG. 13), in such a way that it will come into contact with the detection regions 112 and will then exit through the outlet hole 116. In this way, it is possible to set up bonds between the receptors 111 arranged in the detection regions 112 and target molecules MB (FIG. 13) present in the specimen to be analyzed that flows in the channel 110. It is hence possible cause specific markers 113, such as for example fluorescent markers, to couple with the target molecules that have bound to the receptors, in such a way that these specific markers will label the receptors 111 themselves.

Figure 12:
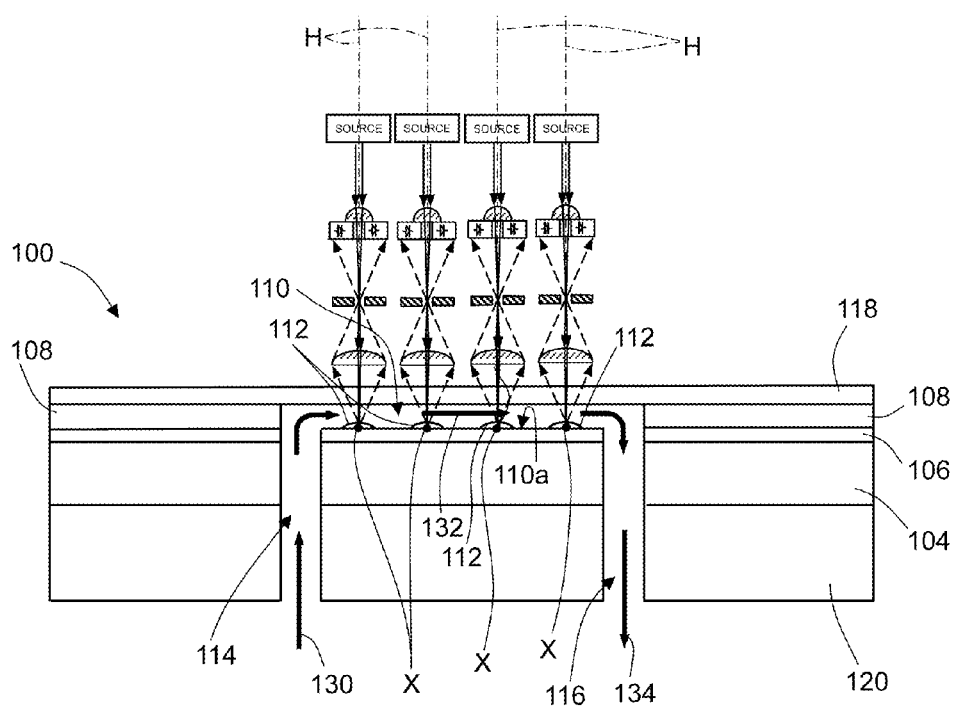
FIG. 12 is a schematic cross-sectional view, taken along the line of cross section XII-XII shown in FIG. 11, of the diagnostic device shown in FIG. 11 and of an array of optical detectors coupled thereto.

Advantageously, the specific markers 113 used within the detection regions 112 are of the type such that, when excited by radiation at the first wavelength $\lambda_1$, emit radiation at the second wavelength $\lambda 2$. Consequently, as shown in FIG. 12, where it is assumed for simplicity that the array 220 is linear, it is possible to arrange the array 220 on top of the diagnostic device 100 in such a way that each optical detector 20 of the array 220 will have the respective image point X that lies within a corresponding detection region 112. The array 220 is hence arranged in such a way that the system axis H of each optical detector 20 will intercept a corresponding detection region 112.

In this way, considering a single optical detector 20 of the array 220, the corresponding light source 22 generates radiation at the first wavelength $\lambda_1$, which impinges in the corresponding detection region 112. If said detection region 112 contains activated markers, they emit radiation at the second wavelength $\lambda_2$, which is received by the optoelectronic sensor 26 of the optical detector considered, as described previously. The intensity of the radiation at the second wavelength $\lambda_2$ detected by the optoelectronic sensor 26 is a function of the amount of markers effectively activated within the corresponding detection region 112, and is hence a function of the bonds effectively set up between the receptors 111 arranged in the detection region 112 and the specimen to be analyzed that flows in the channel 110. Advantageously, in order to increase the radiation at the second wavelength $\lambda_2$ received by the optoelectronic sensor 26, it is possible for the compatible layer 106 to have a thickness equal to an odd multiple of a quarter of the first wavelength $\lambda_1$ divided by the refractive index of the compatible layer 106. Moreover, the compatible layer 106 can be transparent both to the first wavelength $\lambda_1$ and to the second wavelength $\lambda_2$.

Figure 26:
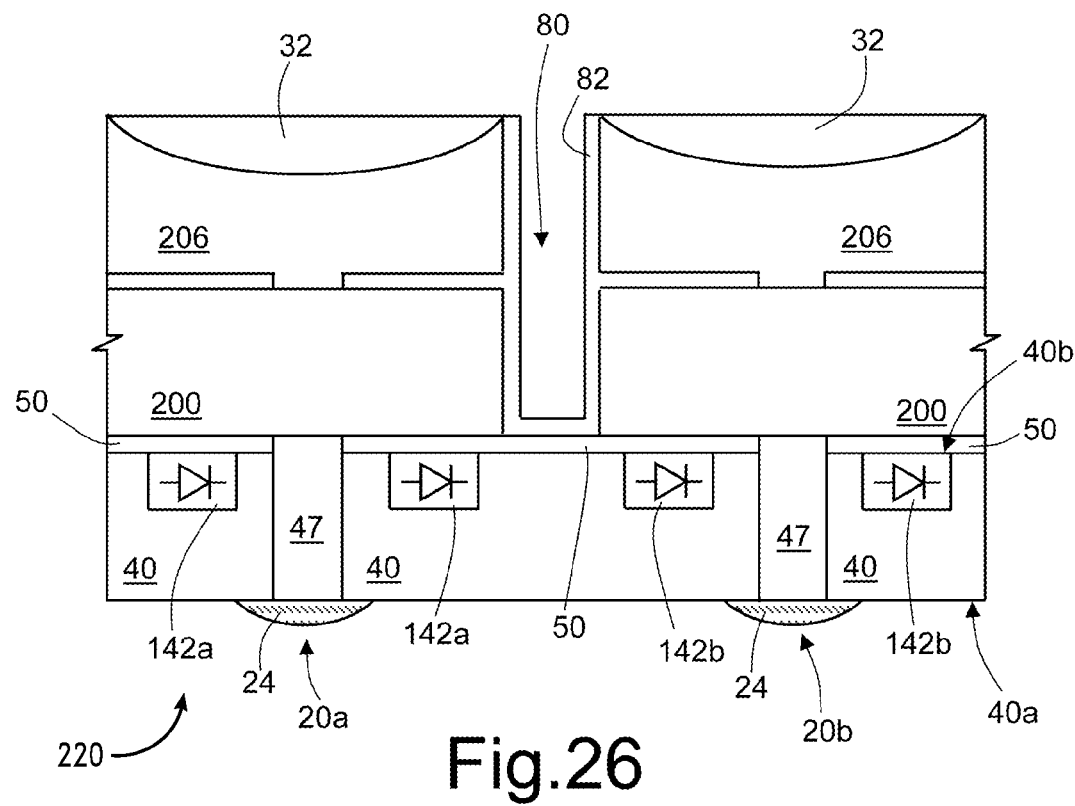

The optical detector 20 may be obtained by applying the manufacturing method described in what follows and is represented in FIGS. 14-26, in which reference is made, by way of example, to an array 220 formed by at least a first optical detector and a second optical detector, here designated by 20a and 20b (FIG. 26).

Figure 14:
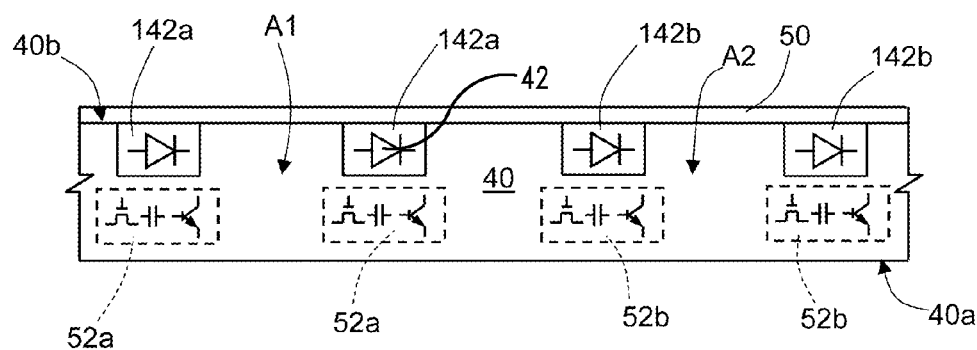
FIGS. 14-26 are schematic cross sections of an array of optical detectors during successive manufacturing steps.
Figure 15:
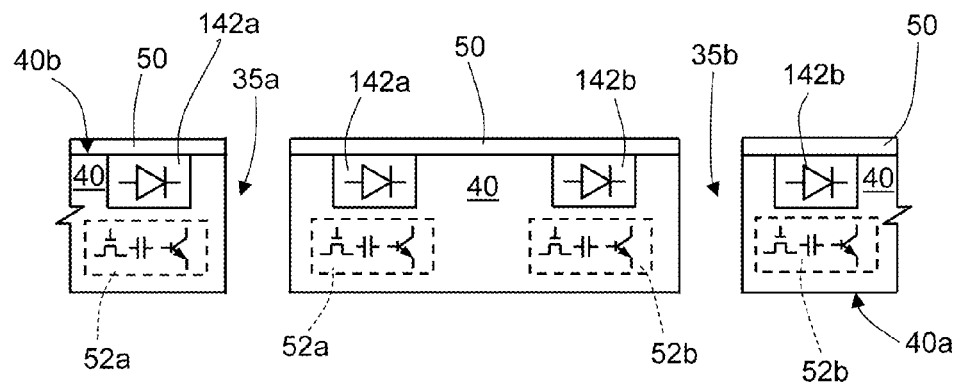
Figure 16:
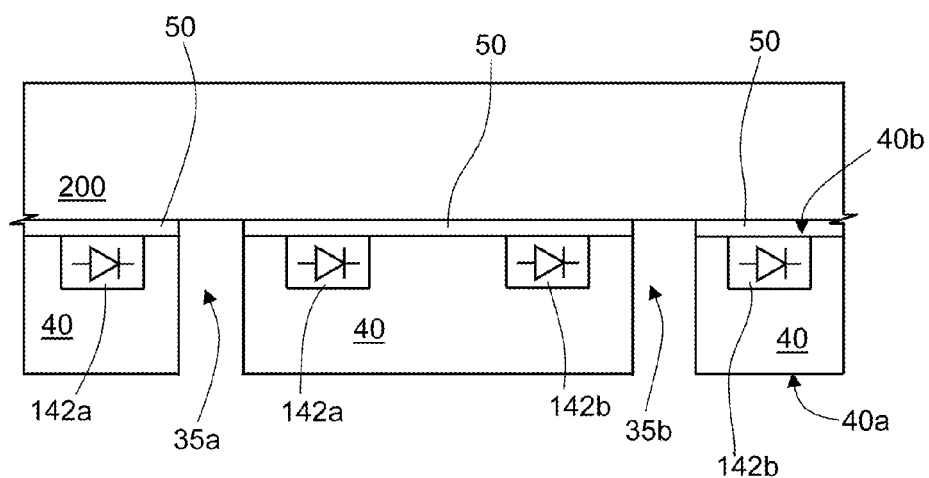
Figure 17:
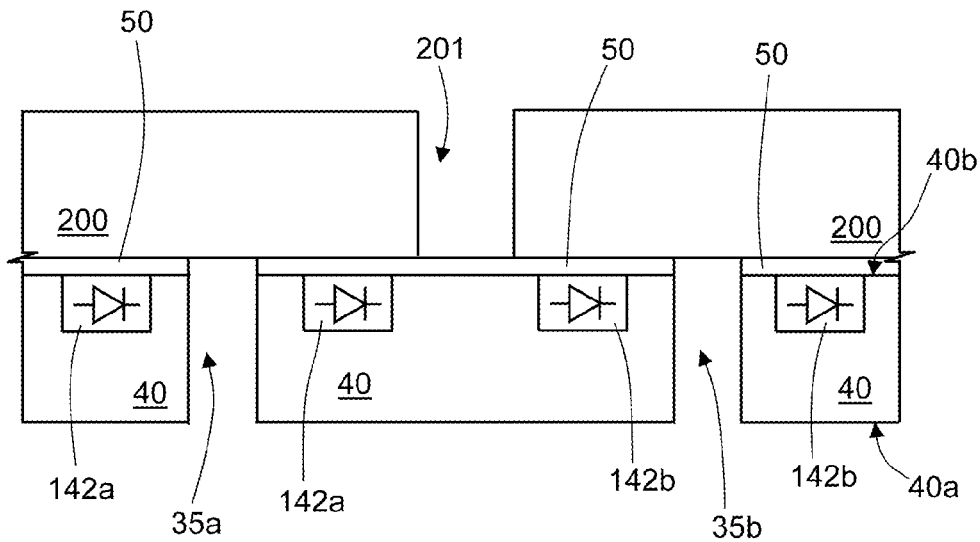
Figure 18:
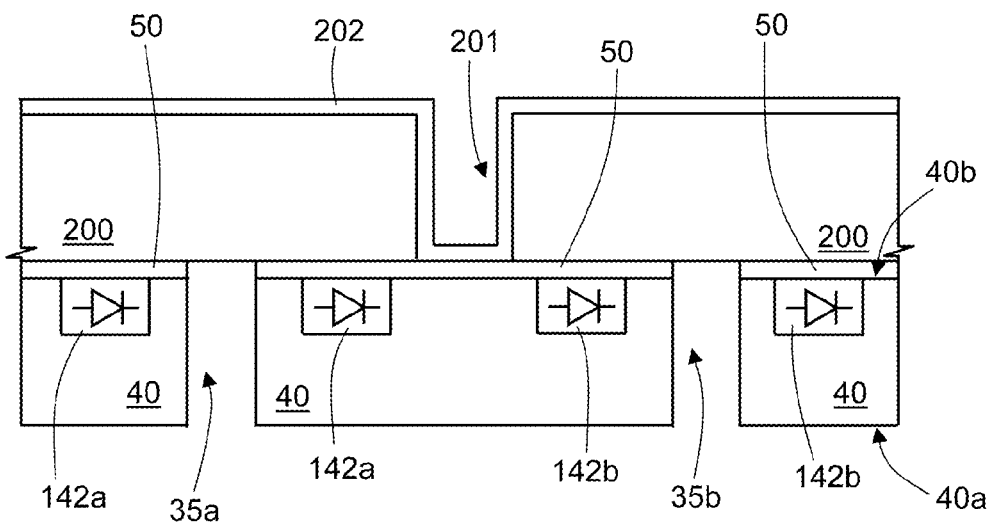
Figure 19:
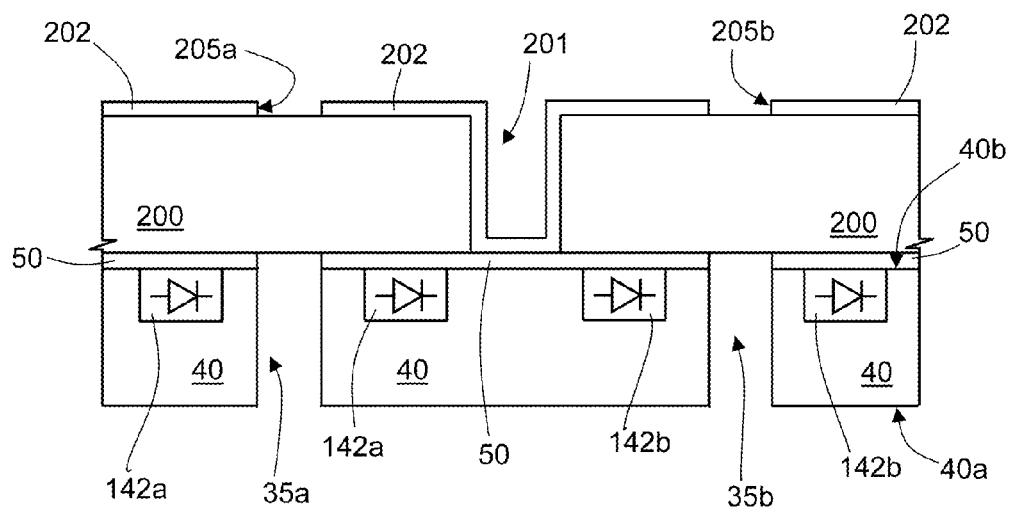

In detail, as shown in FIG. 14, the die 40 is provided, overlaid by the optical filter 50 and housing at least a first detection region 142a and a second detection region 142b, as well as at least a first electronic detection circuit 52a and a second electronic detection circuit 52b. Note that, unlike what is shown for example in FIG. 6, in FIG. 14 and in the subsequent figures the die 40 is oriented in such a way that the first surface 40a will function as bottom surface of the die 40, and the second surface 40b will function as top surface of the die 40.

In greater detail, each between the first detection region 142a and the second detection region 142b houses at least one SPAD 42. In addition, the first detection region 142a and the first electronic detection circuit 52a are arranged within the die 40 so as to define a first area $A_1$, inside which there does not extend any portion of the first detection region 142a or of the first electronic detection circuit 52a. Likewise, the second detection region 142b and the second electronic detection circuit 52b are arranged within the die 40 so as to define a second area $A_2$, inside which there does not extend any portion of the second detection region 142b or of the second electronic detection circuit 52b.

Next (FIG. 15), portions of the optical filter 50 and of the die 40 are selectively removed, for example using the so-called through-silicon-via (TSV) technology, in order to form a first opening 35a and a second opening 35b. In particular, the first and second openings 35a, 35b are formed within the first area $A_1$ and the second area $A_2$, respectively, in such a way as not damage either the first detection region 142a or the second detection region 142b, or the first electronic detection circuit 52a or the second electronic detection circuit 52b. For simplicity of representation, in the subsequent figures the first and second electronic detection circuits 52a, 52b are no longer shown.

Next (FIG. 16), a first dielectric layer 200 is formed on top of the optical filter 50, with which it is in direct contact; the first dielectric layer 200 is hence arranged on top of the top surface 40b. Moreover, the first dielectric layer 200 can be made, for example, of silicon oxide $SiO_2$ and may be provided by means of techniques of chemical vapor deposition (CVD), or else sputtering, or else the so-called "spin-coating" technique.

Next (FIG. 17), an etch is made of the first dielectric layer 200, in order to form a third opening 201, which extends throughout the thickness of the first dielectric layer 200, until part of the optical filter 50 is exposed. By way of example, the etch may be a plasma etch, or else a wet etch.

Next (FIG. 18), a first conductive layer 202 is formed on top of, and in direct contact with, the first dielectric layer 200, for example by sputtering of metal particles. In particular, the first conductive layer 202 is formed so as not to fill the third opening 201 completely, but rather so as to cover the side walls thereof, as well as the bottom, i.e., the delimited portion of the optical filter 50. The first conductive layer 202 forms the opaque layer 30 described above.

Next (FIG. 19), portions of the first conductive layer 202 are selectively removed, for example using techniques of photolithography, in order to form a fourth opening 205a and a fifth opening 205b, which extend throughout the thickness of the first conductive layer 202 and are respectively aligned vertically to the first and second openings 35a, 35b. In particular, the fourth and fifth openings 205a, 205b do not extend through the first dielectric layer 200. The fourth and fifth openings 205a, 205b form the pinhole 30a through the layer 30 as described above.

Figure 20:
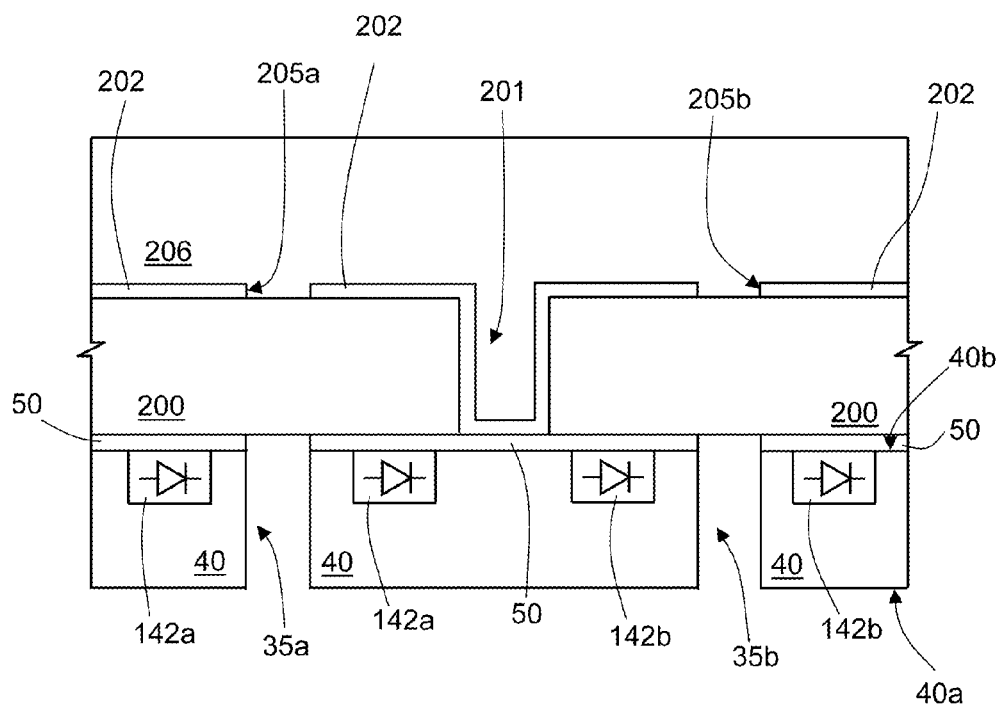
Figure 21:
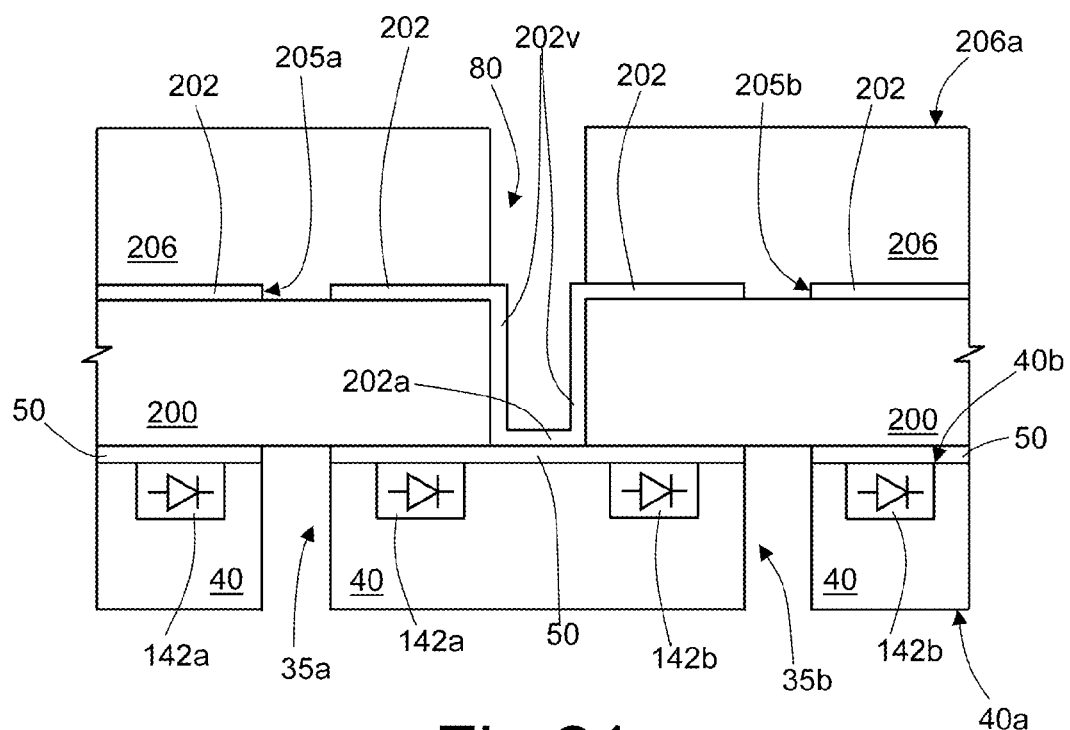
Figure 22:
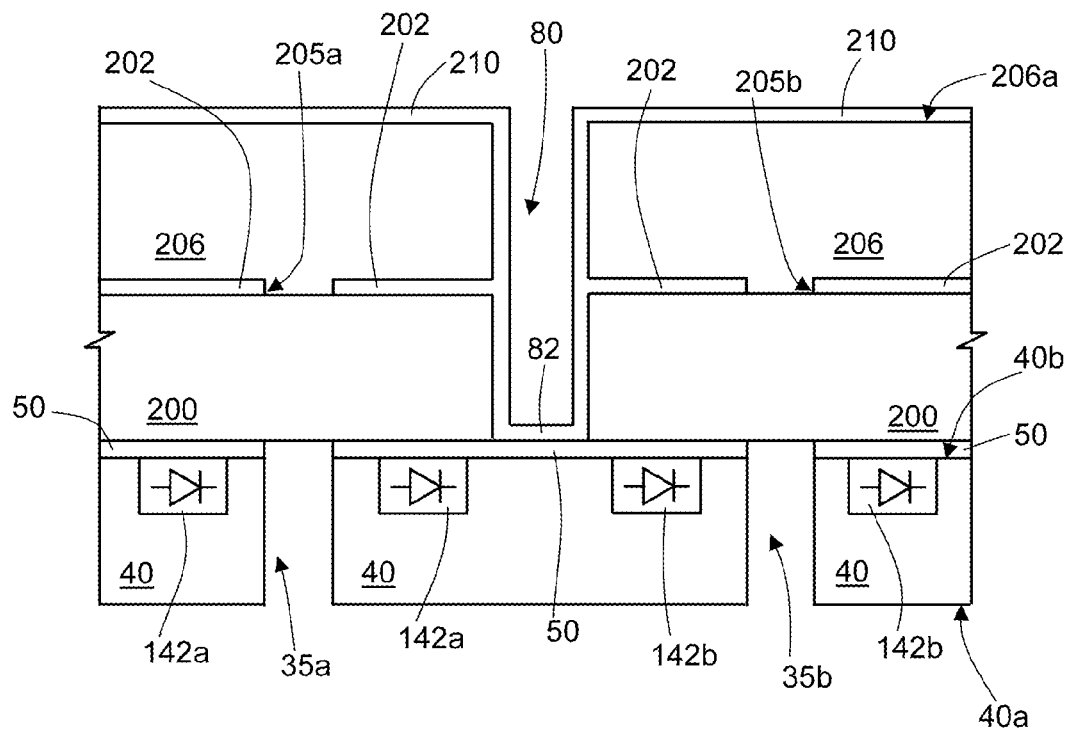
Figure 23:
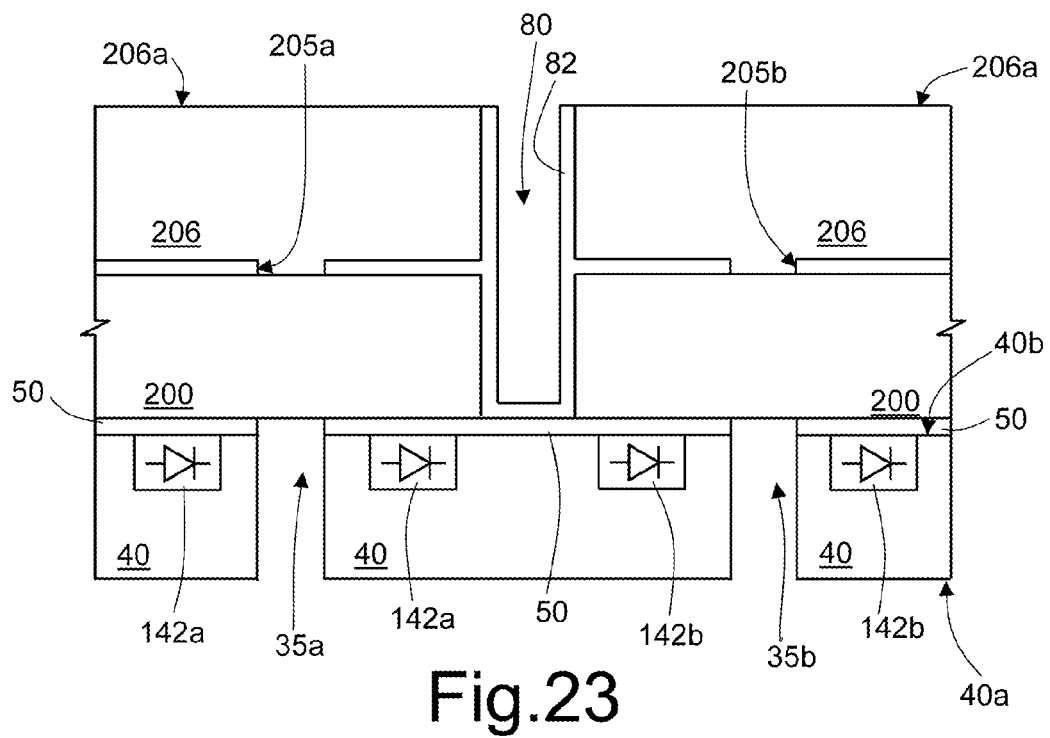
Figure 24:
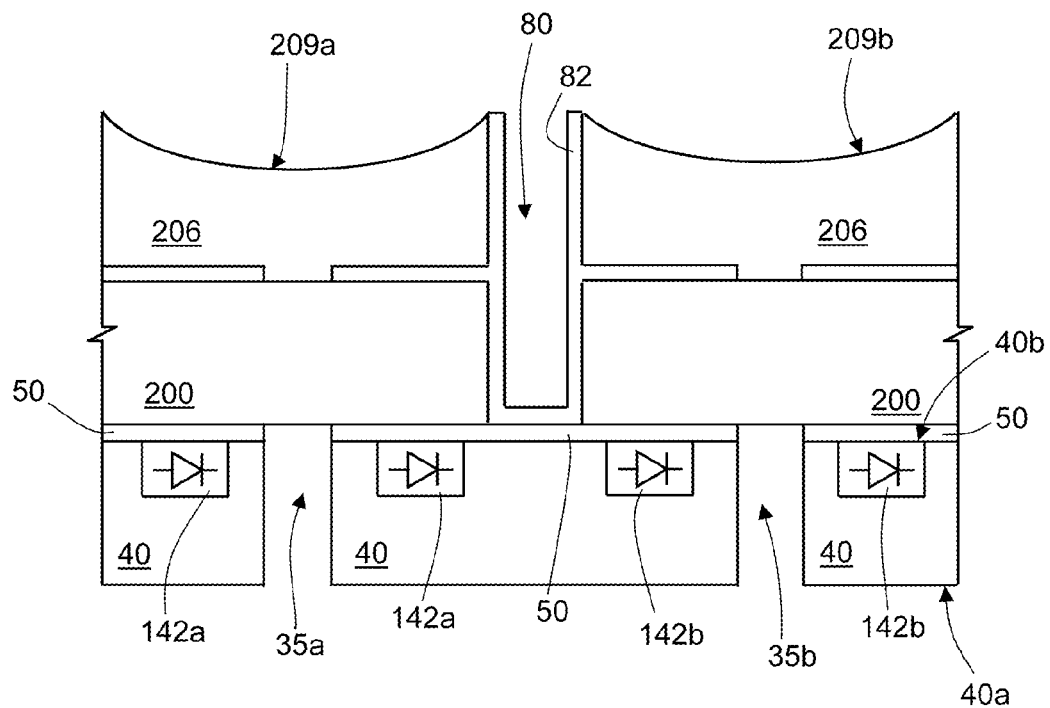
Figure 25:
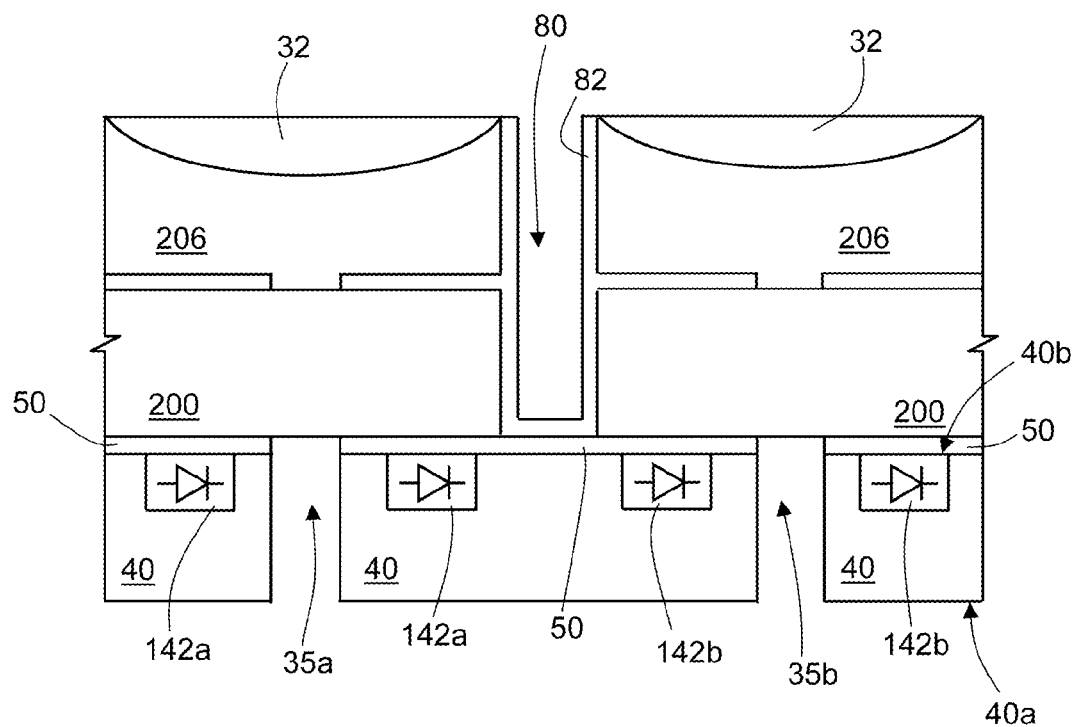

Next (FIG. 20), a second dielectric layer 206 is formed, made, for example, of silicon oxide $SiO_2$ and arranged on top of, and in direct contact with, the first conductive layer 202. In particular, the second dielectric layer 206 may be obtained, for example, by chemical vapor deposition. In addition, the second dielectric layer 206 may extend within the third, fourth, and fifth openings 201, 205a, 205b, until it fills them completely, as shown in FIG. 20. It is, however, possible for the second dielectric layer 206 not to fill completely, for example, the third opening 201. In practice, the first and second dielectric layers 200, 206 form the dielectric region 66 of FIG. 8.

Next (FIG. 21), an etch of the second dielectric layer 206 is performed in order to remove selectively a portion thereof and form the trench 80. In particular, designating by 206a the top surface of the second dielectric layer 206, the trench 80 extends starting from the top surface 206a of the second dielectric layer 206 as far as the first conductive layer 202 on the optical filter 50. In addition, the trench 80 occupies, among other things, the space previously occupied by the third opening 201. Moreover, designating by 202a a first portion of the first conductive layer 202 arranged in direct contact with the optical filter 50, and by 202v a second portion of the first conductive layer 202 arranged vertically, the trench 80 is internally coated by the first and second portions 202a, 202v of the first conductive layer 202. By way of example, the etching to form the trench 80 can be plasma etching, or else wet etching.

Next (FIG. 22), a second conductive layer 210 is formed, for example by means of sputtering of metal particles.

In particular, the second conductive layer 210 is formed on top of the top surface 206a of the second dielectric layer 206, with which it is in direct contact. In addition, the second conductive layer 210 coats internally the trench 80, forming, together with the first conductive layer 202, the opaque coating 82.

Next (FIG. 23), for example by using techniques of photolithography, a portion of second conductive layer 210 arranged on top of the top surface 206a of the second dielectric layer 206, and hence on top of the fourth and fifth openings 205a, 205b, is selectively removed.

Next (FIG. 24), an isotropic etch of the second dielectric layer 206 is made, starting from the top surface 206a thereof, for example by using hydrofluoric acid HF. In this way, the top surface 206a of the second dielectric layer 206 assumes a spherical curvature both over the fourth opening 205a and over the fifth opening 205b, thus defining a first concavity 209a and a second concavity 209b.

Then (FIG. 25) a deposition of antimony trioxide $Sb_2O_3$ is made on top of the second dielectric layer 206, within the first and second concavities 209a, 209b, followed by chemical-mechanical polishing, in order to form two second lenses 32.

In FIG. 26, two first lenses 24 and two transparent regions 47 are hence provided as part of the first and second optical detectors 20a, 20b. The first lenses 24 may be formed with a different process, such as in a different manufacturing facility, and then attached to the array 220. The transparent regions 47 may be formed by depositing a transparent material in the first and second openings 35a, 35b or as described above with respect to FIG. 6. The optical detectors 20a, 20b also include respective light sources (not shown in FIG. 26). In particular, even though it is not shown, it is possible to provide a further die, inside which at least a first light source and a second light source are formed, and to couple this further die to the die 40, for example, by means of a technique known as "wafer-bonding".

The advantages that the present optical detector affords emerge clearly from the foregoing description. In particular, it is characterized by limited overall dimensions and by the consequent ease of integration in an array of small dimensions, enabling parallelization of the operations of analysis of an assay.

Finally, it is evident that modifications and variations may be made to the present optical detector 20, array 220, and manufacturing method, without thereby departing from the scope of the present disclosure.

For example, the dielectric region 66, and consequently the first and second dielectric layers 200, 206, may be made of plastic material, such as for example polycarbonate, or else polyethylene, or else polydimethylsiloxane (PDMS). In this case, in order to form the second lens 32, instead of performing an isotropic etch of the second dielectric layer 206 (FIG. 24), it is possible to carry out a hot embossing, above the temperature of deformation of the plastic material forming the second dielectric layer 206.

In addition, instead of the SPADs 42, the optoelectronic sensor 26 may comprise photodetectors of a different type. For example, the optoelectronic sensor 26 may be formed by a charge-coupled device.

As regards the first lens 24, it may not be in direct contact with the optoelectronic sensor 26. In addition, the opaque coating 82, instead of being made of metal material, may be made of plastic material opaque to the first and second wavelengths $\lambda_1$, $\lambda_2$.

Finally, it is possible for the first lens 24 and/or the second lens 32 to be formed by regions of polymeric material and to be mechanically coupled to corresponding regions of piezoelectric material, which, if subjected to voltages, modify their own geometrical shapes. In particular, the regions of polymeric material may be mechanically coupled to the regions of piezoelectric material in such a way that any modifications of the geometrical shapes of the regions of piezoelectric material induce corresponding modifications of the geometrical shapes of the regions of polymeric material, and in particular induce modifications of the radii of curvature of the regions of polymeric material. Consequently, the first lens 24 and/or the second lens 32 have radii of curvature that are variable in an electronically controllable way.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A confocal optical detector, comprising:
a light source configured to generate a first optical beam along an axis;
an optoelectronic sensor aligned along the axis;
an optical focusing device configured to receive and focus the first optical beam, the optical focusing device being aligned with the optoelectronic sensor along the axis; and
an opaque layer having a hole, the hole being configured to receive the first optical beam, the layer being arranged between the optoelectronic sensor and the optical focusing device, the optoelectronic sensor being arranged between the light source and the layer.

2. The confocal optical detector according to claim 1, wherein the hole of the layer has a center arranged along the axis, and the hole and the optical focusing device are configured to have the center be a conjugate point of an image point with respect to the optical focusing device.

3. The confocal optical detector according to claim 2, further comprising:
a first-focusing stage arranged between the light source and the layer, the first-focusing stage being configured to focus the first optical beam at the center of the hole, wherein:
the optoelectronic sensor is configured to be traversed by the first optical beam;
the optical focusing device is configured to focus the first optical beam, after traversing the hole, at the image point; and
the hole in the layer and the optical focusing device are configured to direct on the optoelectronic sensor a second optical beam to be generated by an element to be analyzed arranged at the image point.

4. The confocal optical detector according to claim 3, wherein the hole in the layer and the optical focusing device are configured to direct the second optical beam along said axis, in direction opposite to the first optical beam.

5. The confocal optical detector according to claim 1, further comprising:
a die having a first surface and a second surface, the die including:
a transparent region extending between the first surface and the second surface, the transparent region being transparent to the first optical beam; and
the optoelectronic sensor.

6. The confocal optical detector according to claim 5, wherein the optoelectronic sensor, the optical focusing device, and the layer are formed in a monolithic way.

7. The confocal optical detector according to claim 6, further comprising a dielectric region extending between the optoelectronic sensor and the optical focusing device, the layer being arranged within the dielectric region.

8. A system, comprising:
an array of optical detectors, each detector including:
a light source configured to generate a first optical beam along an axis;
an optoelectronic sensor aligned along the axis;
an optical focusing device configured to receive and focus the first optical beam, the optical focusing device being aligned with the optoelectronic sensor along the axis; and
an opaque layer having a hole, the hole being configured to receive the first optical beam and being arranged between the optoelectronic sensor and the optical focusing device, and the optoelectronic sensor being arranged between the light source and the layer.

9. The system according to claim 8, further comprising:
a die having a first surface and a second surface, each of the optoelectronic sensors of the detectors being formed in the die, the die including:
a dielectric region extending between the optoelectronic sensor and the optical focusing device of each detector, the hole of each detector being arranged within the dielectric region;
a trench having an interior surface, the trench being arranged between the dielectric regions of adjacent optical detectors; and
an opaque coating formed on the interior surface of the trench.

10. The system according to claim 9 wherein the die includes a transparent region extending between the first surface and the second surface, the transparent region being transparent to the first optical beam.

11. The system according to claim 8, wherein the hole of the layer has a center arranged along the axis, and the hole and the optical focusing device are configured to have the center be a conjugate point of an image point with respect to the optical focusing device.

12. The system of claim 8, further comprising:
a microfluidic diagnostic device that includes:
a substrate;
a compatible layer formed on the substrate, the compatible layer having a first surface;

a structural layer formed on the first surface of the compatible layer, the structural layer having a second surface;

a channel formed in the structural layer, the channel exposing a portion of the first surface of the compatible layer;

a cover layer on the second surface of the structural layer, the cover layer being transparent to the first optical beam and being configured to seal the channel; and a plurality of detection regions on the portion of the first surface of the compatible layer in the channel, the detection regions having receptive molecules configured to detect target molecules;

the array of optical detectors being arranged with the diagnostic device to have each of the image points of the optical detectors be located within a respective detection region.

13. The system according to claim 8, further comprising:

a processing unit, coupled to the array of optical detectors; and a power supply coupled to said processing unit and to said array of optical detectors.

14. A method, comprising:

forming a confocal optical detector, the forming of the detector including:
  providing a light source configured to generate a first optical beam along an axis;
  providing an optoelectronic sensor;
  providing an optical focusing device configured to receive and focus the first optical beam;
  aligning the optoelectronic sensor and the optical focusing device being along the axis;
  providing an opaque layer having a hole, the hole being configured to receive the first optical beam and being arranged between the optoelectronic sensor and the optical focusing device, and the optoelectronic sensor being arranged between the light source and the layer.

15. The method according to claim 14, wherein providing the optoelectronic sensor includes:
  forming a detection region in a substrate, the substrate having a first surface and a second surface, the substrate having a first area and a second area, the forming of the detection region including:
    forming a photodetector,
    forming a first electronic detection circuit, the first detection region and the first electronic detection circuit defining the first area of the substrate; and
  forming a sensor opening through the first area of the substrate, the forming of the sensor opening including:
    selectively removing a portion of the first area;
  forming a hole through a first conductive layer, the forming of the hole including:
    forming a first dielectric layer on the first surface of the die;
    forming the first conductive layer on the first dielectric layer; and
    forming the hole through the first conductive layer, the forming of the hole including:
      selectively removing a portion of the first conductive layer to form the hole, the hole opening being vertically aligned to the sensor opening;
  forming an optical focusing device, the forming of the optical focusing device including:
    forming a second dielectric layer on the first conductive layer;
    forming a concavity in the second dielectric layer; and
    forming the optical focusing device within the concavity, aligned vertically to the hole and to the sensor opening.

16. The method according to claim 15, wherein the first and second dielectric layers include silicon oxide.

17. The method according to claim 15, wherein forming the concavity in the second dielectric layer includes performing an isotropic etch of the second dielectric layer.

18. The method according to claim 15, wherein the first and second dielectric layers include a plastic material.

19. The method according to claim 15, wherein forming the concavity in the second dielectric layer includes performing a hot embossing of the second dielectric layer.

20. The method according to claim 15, further comprising:
  after forming the second dielectric layer and prior to forming the concavity in the second dielectric layer, forming a trench laterally staggered with respect to the sensor opening and to the hole opening, the forming of the trench including:
    selectively removing a portion of the second dielectric layer; and
  prior to forming the concavity in the second dielectric layer, forming a second conductive layer on the second dielectric layer and within the trench; and
  selectively removing a portion of the second conductive layer aligned with the hole opening.

* * * * *